United States Patent
Kvaløy et al.

(10) Patent No.: US 11,944,517 B2
(45) Date of Patent: Apr. 2, 2024

(54) HEARING PROTECTION DEVICE HAVING DOSIMETER WITH ALERTING FUNCTION

(71) Applicant: Minuendo AS, Oslo (NO)

(72) Inventors: Olav Kvaløy, Oslo (NO); Tom Trones, Oslo (NO)

(73) Assignee: Minuendo AS, Oslo (NO)

( * ) Notice: Subject to any disclaimer, the term of this patent is extended or adjusted under 35 U.S.C. 154(b) by 203 days.

(21) Appl. No.: 17/625,357

(22) PCT Filed: Jul. 3, 2020

(86) PCT No.: PCT/GB2020/051609
§ 371 (c)(1),
(2) Date: Jan. 7, 2022

(87) PCT Pub. No.: WO2021/005343
PCT Pub. Date: Jan. 14, 2021

(65) Prior Publication Data
US 2022/0265475 A1    Aug. 25, 2022

(30) Foreign Application Priority Data

Jul. 8, 2019 (GB) .................................... 1909750

(51) Int. Cl.
| | |
|---|---|
| *G10K 11/16* | (2006.01) |
| *A61F 11/08* | (2006.01) |
| *A61F 11/14* | (2006.01) |
| *H04R 1/10* | (2006.01) |

(52) U.S. Cl.
CPC ............ *A61F 11/145* (2022.01); *A61F 11/08* (2013.01); *H04R 1/1083* (2013.01)

(58) Field of Classification Search
CPC ....... A61F 11/145; A61F 11/08; H04R 1/1083
USPC .......................................................... 381/72
See application file for complete search history.

(56) References Cited

U.S. PATENT DOCUMENTS

| | | |
|---|---|---|
| 3,802,535 A | 4/1974 | Peake et al. |
| 4,307,385 A | 12/1981 | Evans et al. |
| 6,456,199 B1 | 9/2002 | Michael |
| 7,401,519 B2 | 7/2008 | Kardous |

(Continued)

FOREIGN PATENT DOCUMENTS

| | | |
|---|---|---|
| WO | 2012071650 A1 | 6/2012 |
| WO | 2018075715 A1 | 4/2018 |

OTHER PUBLICATIONS

International Search Report; European Patent Office; International Application No. PCT/GB2020/051609; dated Sep. 9, 2020; 4 pages.

(Continued)

*Primary Examiner* — William J Deane, Jr.
(74) *Attorney, Agent, or Firm* — Taft Stettinius & Hollister LLP (57) ABSTRACT

A system including an acoustic barrier suitable for wearing in or on an ear of an individual mammalian subject, and a processor. The acoustic barrier defines at least one sound path therethrough and includes a microphone for measuring sound pressure inside the acoustic barrier. The processor is arranged to receive measurements from the microphone and determine a risk that a sound dose limit will be reached before a predetermined time associated with the dose limit. The system is arranged to provide an indication of the determined risk.

20 Claims, 5 Drawing Sheets

(56) References Cited

U.S. PATENT DOCUMENTS

| | | | |
|---|---|---|---|
| 10,068,451 B1* | 9/2018 | Werner | H04R 29/00 |
| 10,764,700 B1* | 9/2020 | Felton | G01H 3/14 |
| 11,228,835 B2* | 1/2022 | Felton | G06F 3/04847 |
| 2007/0214893 A1 | 9/2007 | Killion | |
| 2010/0278350 A1 | 11/2010 | Rung | |
| 2013/0094658 A1* | 4/2013 | Holter | G10K 11/17861 |
| | | | 381/72 |
| 2015/0223000 A1 | 8/2015 | Bran et al. | |
| 2018/0301011 A1 | 10/2018 | Werner et al. | |
| 2018/0359555 A1* | 12/2018 | Jenkins | G01H 3/12 |
| 2019/0073618 A1* | 3/2019 | Kanukurthy | G08B 21/02 |
| 2020/0037060 A1* | 1/2020 | Jenkins | G01H 3/12 |
| 2023/0329913 A1* | 10/2023 | Li | G10L 15/22 |

OTHER PUBLICATIONS

Written Opinion of the International Searching Authority; European Patent Office; International Application No. PCT/GB2020/051609; dated Sep. 9, 2020; 12 pages.

European Examination Report; European Patent Office; European Application No. 20739450.3; dated Jan. 4, 2024; 8 pages.

\* cited by examiner

HEARING PROTECTION DEVICE HAVING DOSIMETER WITH ALERTING FUNCTION

CROSS REFERENCE TO RELATED APPLICATIONS

This application is a U.S. national stage filing of International Patent Application No. PCT/GB2020/051609 filed Jul. 3, 2020, which claims priority to United Kingdom Patent Application No. 1909750.0 filed Jul. 8, 2019, the contents of each application are hereby incorporated by reference in their entirety.

This invention relates to hearing protection, in particular trying to avoid exceeding a sound dose limit.

In a variety of professions, for example construction and performance arts, employees are subjected to high amplitude noises. When exposure to high amplitude noises occurs over an extended period of time, it can result in permanent damage to the function of the ear i.e. to an individual's hearing. As such, appropriate protection against these high amplitude noises is important to reduce the health risk of working in such environments.

Whilst protection, in the form of ear plugs (both active and passive) and over-the-ear defenders, is available to reduce the health risk associated with the exposure to high amplitude noises, this protection may be incorrectly fitted or not worn as appropriate. It is therefore important, even whilst implementing appropriate protection, to monitor the exposure of individuals to high amplitude noises to ensure the individuals' long term safety.

An individual's noise exposure can be calculated and used to ensure they are not exposed to dangerous high amplitude noises over a prolonged period. Accuracy is important, for example a measurement underestimation error of 3 dB is equivalent to underestimating the exposure by half over the course of a day. However, an accurate determination of an individual's noise exposure has previously proved difficult to achieve.

In previous hearing protection devices, mechanisms have been implemented for alerting an individual when a limit of exposure to high amplitude noise has been reached. Receiving such an alert may mean that an individual has to leave the high amplitude noise environment immediately e.g. before the individual has completed their shift.

When viewed from a first aspect, the invention provides a system comprising:
  an acoustic barrier suitable for wearing in or on an ear of an individual mammalian subject, defining at least one sound path therethrough and comprising a microphone for measuring sound pressure inside the acoustic barrier; and
  a processor arranged to receive measurements from said microphone and determine a risk that a sound dose limit will be reached before a predetermined time associated with the dose limit, the system being arranged to provide an indication of said determined risk.

When viewed from a second aspect, the invention provides a method comprising:
  measuring a sound pressure inside an acoustic barrier;
  determining a risk that a sound dose limit will be reached before a predetermined time associated with the dose limit; and
  providing an indication of the determined risk.

Thus, it will be seen that in accordance with the invention a determination is made of the risk to and individual of exceeding a sound dose limit. This may help to reduce the health risk associated with working in environments which result in exposure to high amplitude noises without being significantly detrimental to productivity, as an individual can be alerted if there is a risk that the sound dose limit will be reached before it is actually reached. The individual can then take appropriate action, such as leaving the immediate vicinity of a particular high amplitude noise, properly wearing provided ear protection and/or wearing additional ear protection. Alerting the user to the determined risk allows for an intervention to be made (e.g. implementing additional ear protection) before the sound dose limit is reached, such that the individual does not need to stop working completely e.g. before the end of their shift. This can prevent an individual from sustaining substantial damage to their hearing. In another example, a user in a sound environment above 90 dBA with poorly fitted ear protection may receive an indication of the determined risk that incentivises the user to adjust their ear protection such that it works more effectively.

Traditional dose meters are often attached to clothes, rather than embedded within an acoustic barrier worn by the user on or in their ear in accordance with the present invention. In being attached to the individual's clothes, traditional dose meters have an increased uncertainty in their measurements due to a greater susceptibility to mechanical noise from handling or movement of the embedded microphone. In accordance with the invention, the microphone may be inherently less susceptible to such mechanical noises due to it being protected within the acoustic barrier, and therefore a more accurate measurement of the exposure of an individual to high amplitude noises may be determined.

Using a microphone to measure sound pressure behind the acoustic barrier may also improve the accuracy of the determined risk to the individual as no assumption is required regarding the attenuation of the acoustic barrier. In the traditional dose meters previously described, an estimated attenuation of the hearing protection must be accounted for. These estimations will be inherently inaccurate as they cannot account for variables such as an individual incorrectly positioning the hearing protection such that it does not maximise the attenuation of sound or the individual periodically removing the hearing protection (e.g. to converse with other users or because the hearing protection is uncomfortable). In accordance with the invention, the measurement of the sound pressure behind the acoustic barrier may inherently account for the attenuation of the hearing protection as the microphone is embedded within the hearing device (so as to measure the sound pressure behind the acoustic barrier) and thus the uncertainty in the determined risk is decreased.

Preferably the acoustic barrier is a hearing protection device. When viewed from another aspect the invention provides a hearing protection device suitable for wearing in or on an ear of an individual mammalian subject to form an acoustic barrier, comprising a microphone for measuring sound pressure inside the acoustic barrier and a warning system arranged to determine whether a sound dose limit will be reached based on signals from said microphone and to provide an indication of said determination.

In a set of embodiments, the hearing protection device of any aspect of the invention comprises a device for insertion into an ear canal. An example of such a device is an ear plug. In an alternative set of embodiments, the hearing protection device comprises a device for encompassing the ear of a mammalian subject. An example of such barrier device is a pair of over-the-ear defenders. In certain embodiments, an individual may use both a device for insertion into an ear canal and a device for encompassing the ear. This may be particularly advantageous in extremely high amplitude noise environments, as it increases the overall protection provided.

As will be appreciated by those skilled in the art, the risk of reaching a sound dose limit will be increased if a hearing protection device, typically designed to give substantial attenuation of sound, is incorrectly fitted or not being worn by the individual. The indication provided in accordance with the invention may therefore encourage an individual to ensure their hearing protection is worn and is correctly fitted.

Hearing protection devices provided in accordance with embodiments or aspects of the invention are typically designed to fulfil an important safety role to protect the hearing of an individual in an environment with high amplitude noise. This contrasts with headphones and ear buds, the primary purpose of which is to deliver music, speech or other sound to a user without leakage of sound to the environment or excessive intrusion of ordinary levels of sound from the environment. It follows that such headphones or earbuds are unlikely to provide sufficient attenuation to meet defined safety standards. In a set of embodiments of the present invention the hearing protection device provides a maximum attenuation, when properly fitted and (where applicable) maximally adjusted, of at least 15 dB, e.g. at least 20 dB, e.g. at least 25 dB.

Whilst hearing protection devices may have the ability to deliver limited sound to the user, such as system sounds (e.g. power on, low battery, warnings in accordance with the invention) or speech as part of a communication system, as mentioned above the delivery of sound selected by the user in not their primary purpose. In a set of embodiments therefore the hearing protection device cannot be connected to a user's external sound reproduction device.

In certain embodiments of the present invention, a sound dose is defined to be accrued noise exposure of an individual. The sound dose will take into account that high amplitude sounds causes more damage to an individual hearing than low amplitude sounds. For example, an individual in a low amplitude sound environment will receive a smaller sound dose than an individual who is in a high amplitude sound environment for the same period of time. The sound dose limit may therefore be defined as the maximum sound dose an individual can be subject to before there is a danger of permanent hearing damage. It may be appropriate for the sound dose limit to be different for different individuals. For example, should a particular individual already have substantial permanent damage to their hearing, they may have a lower sound dose limit to ensure there is less risk of additional hearing damage.

The predetermined time associated with the sound dose limit may, in some embodiments, be in the range of e.g. 2-12 hours, e.g. 4-8 hours, e.g. 6 hours. The predetermined time may be prescribed to be equal to the length of a shift of an individual. In environments in which the noise levels are lower, individuals may typically have longer shifts. In environments in which the noise levels are higher, individuals may typically have shorter shifts.

In some embodiments of the invention, the processor is arranged to determined risk that a sound dose limit will be reached by calculating the accrued noise exposure from an initial start time. This accrued noise exposure is representative of the sound dose received by an individual during a current period (e.g. from the start of a shift). The processor may calculate the accrued noise exposure by recording periodic measurement of the sound pressure behind the acoustic barrier. The periodic measurement may be taken every e.g., 5 seconds, 30 seconds, 60 seconds, 5 minutes.

In a set of embodiments, the processor is arranged to predict the estimated total accrued noise exposure by extrapolating the accrued noise exposure. The estimated total accrued noise exposure is noise exposure that it is predicted that an individual will have been exposed to at the predetermined time (e.g. at the end of a shift). The determined risk may then be calculated by the processor based on a comparison between the estimated accrued noise exposure and the sound dose limit. The processor may be arranged to account for at least one other factor in calculating the determined risk. Examples of other factors which may be used to calculate the determined risk include rate of change of accrued noise exposure and the number of instances of a predetermined threshold of amplitude of noise being exceeded in a time period (e.g. one hour). Alternatively, the processor may calculate the determined risk using at least one of these other factors rather than the comparison between the estimated accrued noise exposure and the sound dose limit.

Should the estimated total accrued noise exposure be greater than the sound dose limit, then in a set of embodiments the system is arranged to provide an indication that there is a risk of the sound dose limit being exceeded before the predetermined time is reached.

Whilst the estimated total accrued exposure and/or the accrued noise exposure could be provided to a user, another individual and/or a system, preferably only the indication previously recited herein is provided. The Applicant has recognised that as accrued noise exposure, and in particular the estimated total accrued exposure, may be subject to inherent uncertainties, providing only the risk indication may make the device simpler to use.

The indication of the determined risk can be provided by a number of mechanisms and/or devices. In some embodiments, the system may be arranged to provide a plurality of indications of the determined risk. The plurality of indications may be provided to the user. Alternatively, one or more of the plurality of indications may be provided to another individual or system. The other individual, for example, may be the manager of the user of the system. The manager can then monitor the exposure of the user and adapt their shift if necessary e.g. move them to work in a region with less high amplitude noise or decrease the length of their shift. If an indication is sent to another external system, the indication may be recorded and stored as a record of the individual's exposure over time.

Whilst the indication/all the indications may be provided to another individual or system, preferably at least one indication is provided to the user. This is advantageous as it allows the user to monitor their determined risk independently and take necessary actions as required.

An indication may be provided in a variety of forms. In a set of embodiments, an indication is a visible alert e.g. provided by a light emitting diode, a flashing light or a colour changing light. In another set of embodiments, the indication is an audio alert e.g. a buzzer or a voice message. In another set of embodiments, the indication is a physical alert e.g. a haptic vibration. A physical alert is particularly beneficial in bright environments with high amplitude noise, as the vibrations can be felt on the skin of the individual and thus make it difficult to fail to observe the indication.

In order to provide a physical alert, the system may further comprise a further device. This further device may be a smart-watch or tracker which can produce vibrations to form a physical alert to an individual. There may be other embodiments in which the system comprises a further device. For example, the further device may be a mobile device such as a smartphone or tablet. In such an embodiment, the indication may be in the form of an alert or alarm on the mobile device. The mobile device may include an application which connects to the system described in the first aspect of the invention.

It may be particularly beneficial for the indication to vary depending on the determined risk. For example, in a system where the indication is provided by a light emitting diode, should the risk that the sound dose limit will be reached before the predetermined time associated with the dose limit be low, then a green light may be produced by the LED. Should the risk that a sound dose limit will be reached before the predetermined time associated with the dose limit be moderate, then an amber light may be produced by the LED. Should the risk that a sound dose limit will be reached before the predetermined time associated with the dose limit be high (e.g. the estimated total accrued noise exposure is greater than the sound dose limit), then a red light will be emitted.

The alert may advantageously incentivise the user to take more regular breaks or to employ their hearing protection more often so that they avoid a situation whereby they must end their shift early in order to avoid hearing damage. Should the sound dose limit nonetheless be exceeded before the predetermined time, a more urgent alert may be provided (e.g. the red light may flash) and/or an additional alert may be provided to the individual (and/or their manager) to inform them that they must take immediate action (e.g. leaving the high amplitude noise area). Similarly, different indications may be implemented for other forms of alert (e.g. audio, physical).

In a set of embodiments, the indication provided may be quantitative. For example, an audio alert in the form of a number on an arbitrary scale (e.g. 1-10) may be provided to the individual. A low number (e.g. 2) may indicate that there is a low risk to an individual of exceeding the sound dose limit. A high number (e.g. 9) may indicate that there is a high risk to an individual of exceeding the sound dose limit. In another example, a quantitative indication may be an audible or visual alert indicting the length of time remaining until it is predicted that the sound dose limit will be reached. Such quantitative indication may also be particularly useful in embodiments in which the determined risks are recorded centrally or received by e.g. a manager, as workers could then be co-ordinated (e.g. to lower and higher amplitude noise region) according those these quantitative indications.

Implementing different indications depending on the determined risk can allow the individual to take appropriate action depending on the risk that their sound dose limit will be reached before a predetermined time. For example, the individual may take no action should the indication provided indicate that the determined risk is low; the individual may use the provided hearing protection more diligently when the indication indicates that the determined risk is moderate; or the individual may leave the region of high amplitude noise and/or implement additional protection when the indication indicates that the determined risk is high. The individual therefore has better control over protecting themselves from high amplitude noises.

The Applicant has recognised however that is some circumstances a cruder indication is more appropriate and thus in another set of embodiments only one indication is provided when a certain, predefined determined risk is reached e.g. when the determined risk is high. This may be more effective in encouraging the individual to take immediate action to avoid damage and may prevent confusion, as only one type of alert is provided. Providing too many indications where the determined risk is relatively low may aggravate some individuals and deter them from using the system.

In some embodiments a further warning is provided to an individual upon a change in the situation e.g. upon entering a region with high amplitude noises. This would allow the individual to take precautionary action, such as implementing some or additional ear protection when there is a change in situation or environment.

Providing an indication may encourage a user to take action to protect themselves from high amplitude noises, for example by leaving the immediate vicinity of a particular high amplitude noise, ensuring a correct fit of the hearing protection device and/or wearing additional ear protection.

In a set of embodiments the degree of attenuation provided by the acoustic barrier is adjustable. This could be done manually upon receipt of the indication but in a set of embodiments, the system is arranged to adjust an attenuation provided acoustic barrier in response to a determined risk. For example, the system may be arranged to close or at least partially close a sound path when there is a high risk that a sound dose limit will be reached before a predetermined time associated with the dose limit. This may help prevent users from sustaining hearing damage, as the system actively compensates protection provided in response to the high amplitude noise environments.

It has been appreciated that adjusting the degree of attenuation provided by the acoustic barrier in response to the determined risk is novel and inventive in its own right. Thus when viewed from another aspect the invention provides a system comprising a hearing protection device suitable for wearing in or on an ear of an individual mammalian subject, defining an acoustic barrier and comprising a microphone for measuring sound pressure inside the acoustic barrier; the system further comprising a processor arranged to receive measurements from said microphone and determine a risk that a sound dose limit will be reached, the system being arranged to adjust an attenuation provided by the acoustic barrier dependent on said determination.

It will be appreciated that the optional features of any aspect of the present invention may also be optional features of any other aspect of the present invention disclosed.

Figure 1:
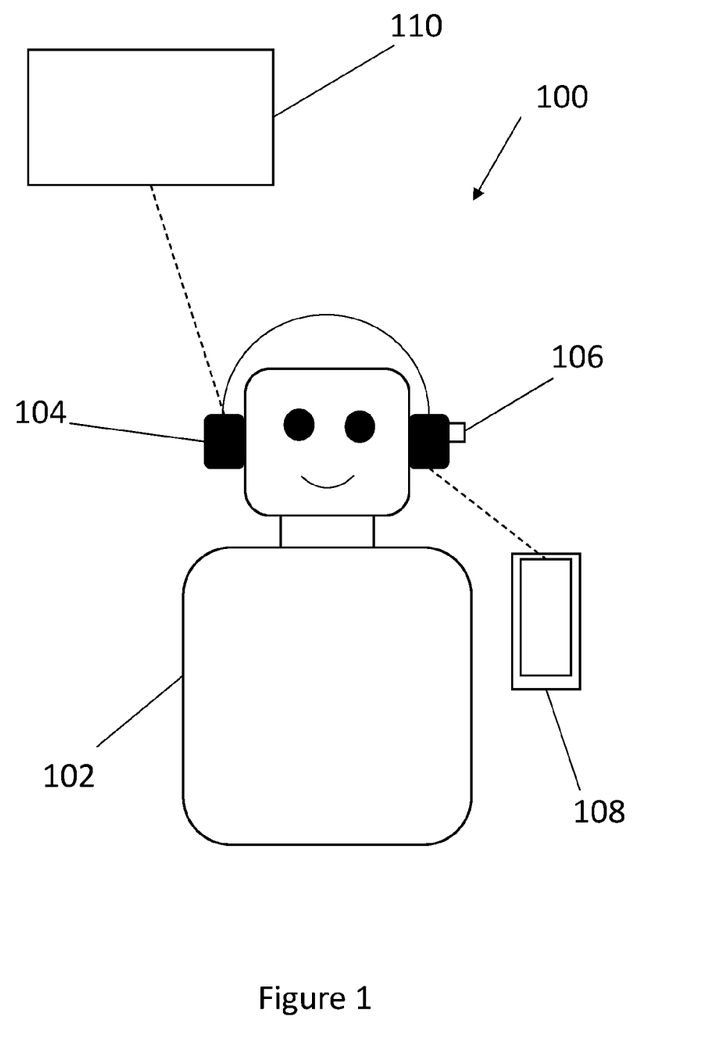
FIG. 1 shows a user implementing a system as described in the form of an over-the-ear acoustic barrier.

A selection of embodiments of the present invention will now be described, by way of example only, with reference to the accompanying drawing in which:

FIG. 1 is an exemplary embodiment of a system 100 in accordance with the present invention for use by an individual 102 in a high amplitude noise environment. The individual may be an employee who regularly works in a high amplitude noise environment e.g. a construction worker, sound technician, warehouse worker, musician, tree surgeon etc.

The individual is provided with an acoustic barrier device in the form of a pair of over-the-ear defenders 104 to help to protect against damage to their hearing resulting from exposure to high amplitude noise over a prolonged period of time. The pair of over-the-ear defenders 104 enclose the entire ears of the individual 102 and thus provide the acoustic barrier. More details can be found below in relation to FIG. 2.

In accordance with the invention and as described in more detail below, the system 100 is arranged to measure exposure to sound and to calculate a risk that sound exposure limit will be reached before a predetermined time—e.g. the end of their shift. A number of devices for indicating the determined risk are provided in this embodiment but only one or fewer of these may be used and other ways of indicating this risk not described could be implemented instead.

As shown in FIG. 1, the over-the-ear defenders 104 comprise a light 106. The light 106 may be a light emitting diode or a small filament bulb. This light provides an indication to workers or supervisors in the vicinity of the individual 102 of the individual's determined risk. For example, the light 106 being on may indicate that the individual's determined risk is above a certain threshold e.g. that the user is expected to exceed the sound dose limit before the end of their shift. Alternatively, the light 106 turning on may indicate to others that more drastic action needs to be taken e.g. that the individual has exceeded the sound dose limit (before the end of their shift) and need to leave the high amplitude noise region immediately. The light 106 may also in some embodiments emit different coloured light depending on the determined risk.

The system 100 further includes a mobile device 108. This mobile device 108 may belong to the individual 102, but could in other embodiments belong to other personnel (e.g. the individual's manager). The over-the-ear defenders may have a built-in processing unit (not seen in FIG. 1) which is arranged to transmit information regarding the determined risk to the mobile device 108. The mobile device 108 can then provide an alert to the user via, for example, an application on the mobile device 108. The mobile device 108 may be configured to provide a haptic alert to an individual 102. In other examples, the processing unit (not shown in FIG. 1) is provided by the mobile device 108. Such a mobile application may receive transmitted relevant information from the over-the-ear protection device 104 (e.g. sound pressure measured behind the acoustic barrier, accrued noise exposure), and use this information to calculate the determined risk using specialist algorithms.

In a similar manner to that described for the light 106 provided on the over-the-ear protection, the mobile device 108 may be configured to provide different alerts depending on the determined risk. For example, a vibration may be provided to alert the user that the determined risk has exceeded a certain predetermined threshold. In a complementary or alternative embodiment, the mobile device 108 may persistently vibrate when the determined risk has exceeded a certain predetermined threshold and/or when individual has exceeded the sound dose limit (before the end of their shift). The vibration may persist until the individual 102 interacts with the mobile device 108 to acknowledge they have received the alert.

The system 100 further comprises a central database 110. The processor in the over-the-ear protection 104 may transmit information e.g. the sound pressure measured inside the acoustic barrier, accrued noise exposure or determined risk, to the central database 110. The central database 110 can record this information relating to the exposure of an individual 102 to high amplitude noises. The recorded information can be used to track the individual's exposure over a longer period of time. It may also allow the individual 102 or other relevant personnel (e.g. the individual manager) access to this information.

Figure 2:
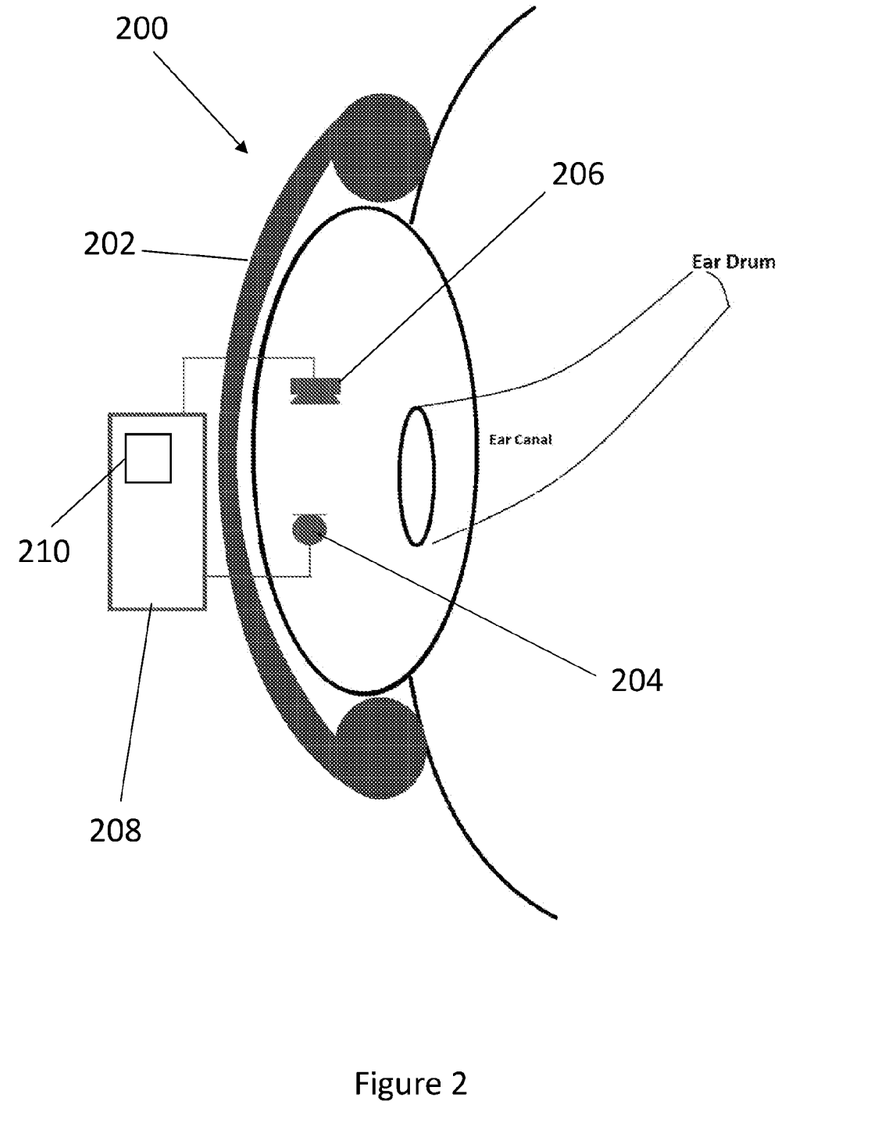
FIG. 2 shows an exemplary over-the-ear acoustic barrier device.

There are a number of different components which may comprise the pair of over-the-ear defenders. FIG. 2 show an exemplary cross-section of one of a pair of over-the-ear defenders 200.

The over-the-ear defender 200 shown in FIG. 2 comprises an outer layer 202 which is intended to provide an acoustic barrier and thus reduce the sound pressure level inside the acoustic barrier compared with outside the acoustic barrier. The over-the-ear defender 200 further comprises a microphone 204 behind the acoustic barrier, a loudspeaker 206 also behind the acoustic barrier and a processing unit 208.

The microphone 204 measures the sound pressure behind the acoustic barrier 202. The microphone 204 may continuously record the sound pressure or may only be actively powered and record the sound pressure at certain time intervals (e.g. every minute). The microphone provides the measurement of the sound pressure level to the processing unit 208.

The processing unit 208 then uses the measurement of the sound pressure level to calculate the determined risk. This calculation is discussed in more detail in relation to the method shown in FIG. 4. In the example shown in FIG. 2, the processing unit 208 comprises a transmitter 210. The transmitter 210 can transmit information such as the measured sound pressure level behind the acoustic barrier or the determined risk to a further device such as a smartwatch, tracker or mobile phone which may then provide an alert to the individual. The transmitter 210 may also transmit such information to a central database as previously described.

The over-the-ear defenders 200 shown in FIG. 2 also comprise a loudspeaker 206. The loudspeaker 206 is used to provide an indication to the individual on the determined risk. This could be in the form a tone indicating when a certain determined risk is reached. Alternatively, the loudspeaker 206 could be used to provide a quantitative alert such as an audio alert indicting the length of time remaining until it is predicted that the sound dose limit will be reached. The loudspeaker 206 may also be used for additional features of the over-the-ear defenders 200 such as playing music, communicating with other workers etc.

Although a user not wearing the ear defenders when they should be may not hear an audible alert, typically the defenders are nonetheless worn around the neck or on top of the head and as such an alert (or combination of alerts) may nonetheless be perceived.

Whilst the acoustic barrier in FIG. 1 is provided by a pair of over-the-ear defenders 104, the acoustic barrier could instead be provided by a device for insertion into the ear canal of the individual 102 and the system 100 would function in the same manner. An example of such a device is shown in FIG. 3.

Figure 3:
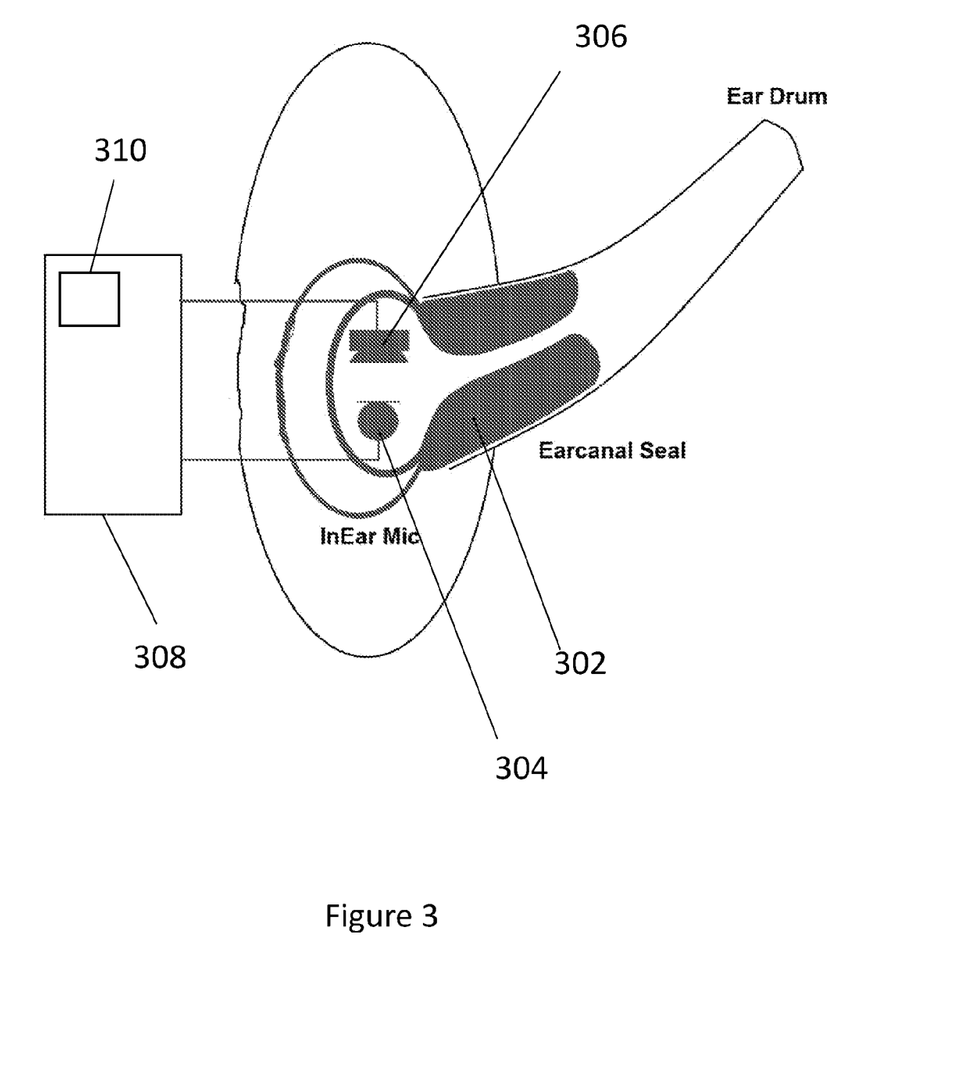
FIG. 3 shows an exemplary in-ear acoustic barrier device.

The device seen in FIG. 3 is an earplug 302 which creates a seal within the ear canal of the individual. The earplug 302 comprises a microphone 304, a loudspeaker 306 and a processing unit 308. These components perform similar functions to those previously described in relation to the over-the-ear protection seen in FIG. 2. However, the processing unit 308 may in certain embodiments not be in the earplug 302 but may be located elsewhere e.g. in a mobile device, elsewhere on the user. This may be necessary due to restraints of dimensions and therefore number of components that can be contained within the ear-plug 302.

Figure 4:
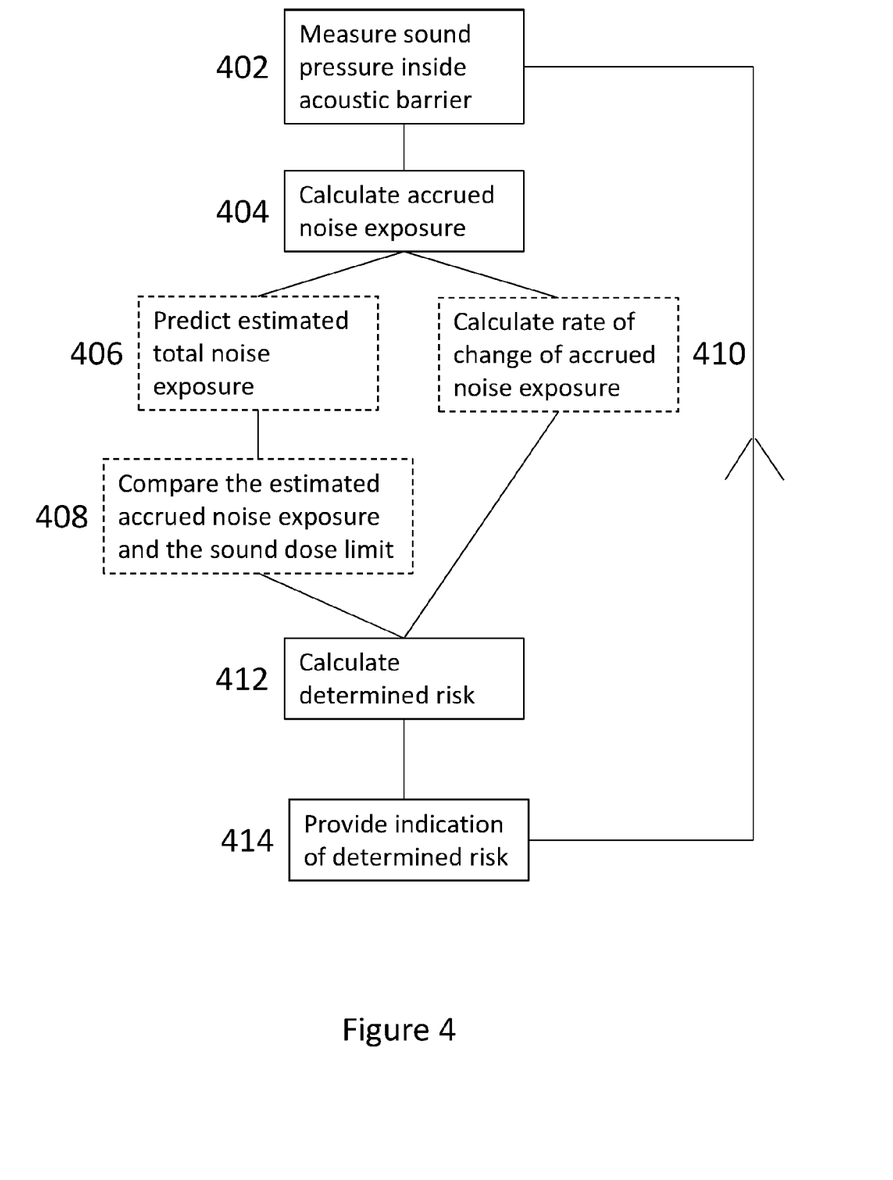
FIG. 4 shows an exemplary method of providing an indication of the determined risk.

FIG. 4 is a flow diagram showing an exemplary method for estimating a risk of a predefined sound exposure dose being reached prematurely and providing an indication to an individual of the determined risk. The method shown in FIG. 4 could be implemented in any system previously described or indeed any other suitable system.

In step 402, the sound pressure inside the acoustic barrier is measured. This measurement is provided by the microphone 204, 304 in the over-the-ear protection 200 or earplug 302 depending on the system implemented. This sound measurement may be made periodically (e.g. every minute) or in other embodiments may be made continuously. The measurement of the sound pressure is then transmitted to the processing unit 208, 308. The processing unit 208, 308 can store the measured sound pressure.

In step 404, the processing unit calculates the accrued noise exposure from the stored measurements of sound pressure. In step 406, the processing unit 208, 308 then extrapolates the accrued exposure to predict the estimated total noise exposure (e.g. that the individual will have experienced by the end of their shift). In step 408, the estimated accrued noise exposure is then compared to the sound dose limit (of the individual). The processing unit 208, 308 then calculates the risk of the limit being reached too soon based on the comparison between the estimate accrued noise exposure.

In some embodiments, the processing unit may also perform the step 410 of calculating the rate of change of accrued noise exposure. This can be an important factor to account for changes in the environment of the individual. For example, the amplitude of the noise in the high amplitude noise environment may steadily increase over a period of time. As the amplitude of the noise increases, the noise exposure of an individual will increase faster. Therefore, should the rate of change of accrued noise exposure not be taken into account, then a determined risk calculated solely on the estimated total noise exposure could be an underestimate.

In step 414 the processor configures an indication of the determined risk which is provided to the individual. This determined risk could be provided to the individual via any of the mechanisms previously described. The indication of the determined risk may be transmitted by a transmitter 210, 310 to a device providing the indication.

A more detailed exemplary algorithm for predicting when a dose limit will be reached will now be described with reference to FIG. 5. This shows a graph of A-weighted sound pressure exerted on the ear drum of an individual versus time. The noise exposure dose, E is defined by Equation 1 as shown below. $p_A$ is the A-weighted sound pressure and t is time. An A-weighted pressure weights the relatively loudness of sounds in air as perceived by the human ear.

$$E = p_A^2 t \qquad [\text{Eq.1}]$$

More accurately the exposure E is the integral of the square of the weighted sound pressure level over time. The noise exposure dose is defined in units of $Pa^2$ hours. 1 $Pa^2$ hour is typically equivalent to an average allowable daily dose for an individual. This is equivalent to being subjected to an average sound pressure of 85 dBA for 8 hours. Some areas of legislation (onshore, offshore, mining, aviation, different countries) may have other daily limits than 1 $Pa^2$ hour. In these cases, a relevant alternative value will be used in the calculation. In the following example, 1 $Pa^2$ hour is taken to the average allowable daily dose.

Figure 5:
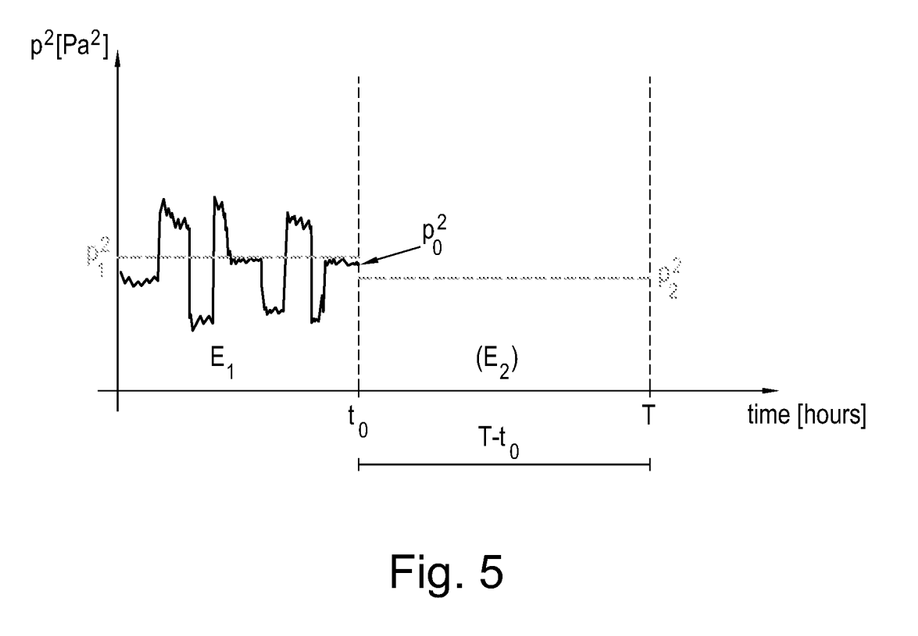
FIG. 5 shows a graph of squared pressure against time.

With reference to the graph shown in FIG. 5, this shows the recorded squared pressure $p^2$ against time, where $p_0^2$ is the squared pressure at the present time to. The total length of the shift is T hours. The variable $p_1^2$ is the average of the pressure history from a start time to $t_0$. $E_1$ is the actual accrued dose from the start time until the present time to and is the area under the curve from the start time to $t_0$. $E_2$ is the amount of exposure that the user is permitted to experience during the rest of the shift to exactly meet the daily dose, as given by Equation 2.

$$E_2 = 1 \text{ Pa}^2 \text{ hour} - E_1 \qquad [\text{Eq.2}]$$

From Equation 1 and Equation 2, a pressure level $p_2^2$ can be calculated which is the maximum continuous pressure an individual can experience for the duration of the shift if the sound dose limit is not to be exceeded. Since the sound pressure level typically varies during a shift, any instantaneous measured sound pressure level may be over or under this particular level without necessarily causing the total dose to be exceeded. Therefore, the system needs to continuously evaluate and predict whether the varying levels will result in an exposure greater than the sound dose limit. The system may then provide an alert indicating that the user needs to take action e.g. improve the fit of their hearing protection or implement additional hearing protection.

Depending on the value of $E_2$ and the current sound pressure $p_0$, the individual may receive a number of alerts. If $E_2$ is less than or equal to zero, then the individual may receive an alert in the form of a red light that indicates that the sound dose limit has already been exceeded (and e.g. the individual must end their shift in the high amplitude noise environment immediately). If $E_2$ is greater than zero, and $p_0^2$ is greater than $p_2^2$ as shown in FIG. 5, then the individual receives an alert in the form of an orange light which indicates that they are expected to exceed the sound dose limit before the end of their shift (e.g. 8 hours). This may encourage the individual to move to a different environment, or take further precautions as implementing (additional) ear protection. If $E_2$ is greater than zero, and $p_0^2$ is less than $p_2^2$, this indicates that the individual does not need to be alerted as the sound dose limit should not the exceeded. This could be indicated to the individual by a green light. More advanced methods may be required to ensure an individual is not alerted too frequently.

Thus it will be appreciated by those skilled in the art that a hearing protection system according to embodiments of the present invention may help to reduce damage to hearing caused by high amplitude noise environments. It will be further appreciated however that many variations of the specific arrangements described herein are possible within the scope of the invention as defined in the claims.

The invention claimed is:

1. A hearing protection device suitable for wearing in or on an ear of an individual mammalian subject to form an acoustic barrier, comprising a microphone for measuring sound pressure inside the acoustic barrier and a warning system arranged to determine whether a sound dose limit will be reached based on signals from said microphone wherein said warning system is arranged to calculate a determined risk using a number of instances of a predetermined threshold of amplitude of noise being exceeded in a time period and to provide an indication of said determination whether a sound dose limit will be reached.

2. The hearing protection device as claimed in claim 1, wherein the hearing protection device comprises a device for insertion into an ear canal.

3. The hearing protection device, as claimed in claim 1, wherein the hearing protection device provides a maximum attenuation of at least 15 dB.

4. The hearing protection device, as claimed in claim 1, wherein the hearing protection device cannot be connected to a user's external sound reproduction device.

5. The hearing protection device, as claimed in claim 1, wherein the processor or warning system is arranged to calculate an accrued noise exposure from an initial start time.

6. The hearing protection device, as claimed in claim 5, wherein the processor or warning system is arranged to calculate the accrued noise exposure by recording periodic measurements of the sound pressure behind the acoustic barrier.

7. The hearing protection device, as claimed in claim 5, wherein the processor or warning system is arranged to predict an estimated total accrued noise exposure by extrapolating the accrued noise exposure and comparing the estimated accrued noise exposure and the sound dose limit.

8. The hearing protection device, as claimed in claim 1, wherein the processor or warning system is further arranged to calculate the determined risk using a rate of change of accrued noise exposure.

9. The hearing protection device, as claimed in claim 1, arranged to provide an indication when there is a risk of the sound dose limit being exceeded before a predetermined time is reached.

10. The hearing protection device, as claimed in claim 1, arranged to provide one or more indications to an individual or system other than the user.

11. The hearing protection device, as claimed in claim 1, comprising a further device arranged to provide the indication in the form of an alert.

12. The hearing protection device, as claimed in claim 1, wherein only one indication is provided when a predefined determined risk is reached.

13. The hearing protection device, as claimed in claim 1, arranged to adjust an attenuation provided by the acoustic barrier in response to a determined risk.

14. A method comprising:
measuring a sound pressure inside an acoustic barrier;
determining a risk that a sound dose limit will be reached before a predetermined time associated with the dose limit by using a number of instances of a predetermined threshold of amplitude of noise being exceeded in a time period; and
providing an indication of the determined risk.

15. The method as claimed in claim 14, further comprising calculating an accrued noise exposure from an initial start time.

16. The method as claimed in claim 15, wherein calculating the accrued noise exposure comprises recording periodic measurements of the sound pressure behind the acoustic barrier.

17. The method as claimed in claim 15, further comprising predicting an estimated total accrued noise exposure by extrapolating the accrued noise exposure and comparing the estimated accrued noise exposure and the sound dose limit.

18. The method as claimed in claim 14, further comprising determining the risk using a rate of change of accrued noise exposure.

19. The method as claimed in claim 14, comprising providing an indication that there is a risk of the sound dose limit being exceeded before the predetermined time is reached.

20. The method as claimed in claim 14, comprising adjusting the attenuation provided by the acoustic barrier in response to the determined risk.

* * * * *